United States Patent
Van Der Graaf et al.

(10) Patent No.: US 8,888,745 B2
(45) Date of Patent: Nov. 18, 2014

(54) APPLICATOR FOR INSERTING AN IMPLANT

(75) Inventors: Iris Epkjen Hobo Van Der Graaf, Deventer (NL); Maurice Petrus Wilhelmus Tak, Hengelo (NL); Juergen Schmidt, Herten (DE); Hendricus Johannes Vertegaal, Hengelo (NL)

(73) Assignee: Merck Sharp & Dohme B.V., Haarlem (NL)

( * ) Notice: Subject to any disclaimer, the term of this patent is extended or adjusted under 35 U.S.C. 154(b) by 220 days.

(21) Appl. No.: 11/795,796

(22) PCT Filed: Jan. 20, 2006

(86) PCT No.: PCT/EP2006/050328
§ 371 (c)(1),
(2), (4) Date: Apr. 2, 2008

(87) PCT Pub. No.: WO2006/077242
PCT Pub. Date: Jul. 27, 2006

(65) Prior Publication Data
US 2008/0221510 A1  Sep. 11, 2008

(30) Foreign Application Priority Data
Jan. 24, 2005  (EP) .................................. 05100419

(51) Int. Cl.
*A61M 5/32*  (2006.01)
*A61M 37/00*  (2006.01)

(52) U.S. Cl.
CPC ................................ *A61M 37/0069* (2013.01)
USPC ............ 604/162; 604/63; 604/64; 604/93.01; 604/288.01; 604/891.1; 604/502; 604/57; 604/59; 604/60; 604/115; 604/130; 604/131; 604/194; 604/232; 604/272; 606/107; 606/108; 227/52; 227/175.1

(58) Field of Classification Search
CPC ...... A61D 7/00; A61M 5/32; A61M 37/0009; A61M 31/00; A61M 39/0208; A61M 5/425; A61M 5/427; A61M 5/46; A61M 5/20; A61M 5/14566; A61M 5/322; A61M 5/24; A61M 5/3286; A61M 2/1664; A61M 2/95; A43D 100/02
USPC ................. 604/60, 64, 93.01, 288.01, 891.1, 604/288.04, 502, 57, 59, 115–117, 130, 604/131, 194, 232, 272; 606/107, 108; 227/52, 175.1
See application file for complete search history.

(56) References Cited

U.S. PATENT DOCUMENTS

| 1,655,158 A | 1/1928 | Muir |
| 3,016,895 A * | 1/1962 | Sein ............................ 604/60 |

(Continued)

FOREIGN PATENT DOCUMENTS

| EP | 0304107 | 2/1989 |
| EP | 596161 | 5/1994 |

(Continued)

OTHER PUBLICATIONS

Croxatto. "Clinical profile of Implanon: a single-rod etonogestrel contraceptive implant." Eur J Contracept Reprod Health Care. Sep. 2000;5 Suppl 2:21-8.*

*Primary Examiner* — Scott Medway
(74) *Attorney, Agent, or Firm* — Hoyng Monegier LLP; David P. Owen; Minerva Rivero

(57) ABSTRACT

The invention pertains to an applicator (1) for inserting an implant, in particular a rod-like implant (2) containing an active substance, under the skin of a human or animal, comprising a housing (3), a cannula (6) extending from the housing (3), and a handle (15) for grasping and maneuvering the applicator (1) and the cannula (6) during insertion of an implant (2). In accordance with the invention, the handle (15) extends above at least part of the length of the cannula (6). Such a handle facilitates insertion of the cannula and/or accurate positioning of the implant.

20 Claims, 4 Drawing Sheets

(56) References Cited

U.S. PATENT DOCUMENTS

| | | | |
|---|---|---|---|
| 3,538,916 A * | 11/1970 | Groff et al. | 604/63 |
| 3,620,216 A * | 11/1971 | Szymanski | 604/60 |
| 3,669,104 A * | 6/1972 | Wyatt et al. | 604/61 |
| 3,766,915 A * | 10/1973 | Rychlik | 604/161 |
| 4,105,030 A * | 8/1978 | Kercso | 604/506 |
| 4,223,674 A | 9/1980 | Fluent et al. | |
| 4,597,753 A * | 7/1986 | Turley | 604/61 |
| 4,834,708 A | 5/1989 | Pillari | |
| 4,871,094 A * | 10/1989 | Gall et al. | 222/386 |
| 4,882,166 A * | 11/1989 | Graham et al. | 424/462 |
| 4,994,028 A * | 2/1991 | Leonard et al. | 604/60 |
| 5,053,014 A * | 10/1991 | Van Heugten | 604/167.03 |
| 5,147,295 A * | 9/1992 | Stewart | 604/61 |
| 5,192,273 A * | 3/1993 | Bierman | 604/174 |
| 5,250,026 A * | 10/1993 | Ehrlich et al. | 604/60 |
| 5,613,954 A * | 3/1997 | Nelson et al. | 604/167.03 |
| 5,697,914 A * | 12/1997 | Brimhall | 604/177 |
| 5,725,497 A * | 3/1998 | Woodruff et al. | 604/506 |
| 5,984,890 A * | 11/1999 | Gast et al. | 604/60 |
| 6,190,350 B1 * | 2/2001 | Davis et al. | 604/61 |
| 6,402,716 B1 | 6/2002 | Ryoo et al. | |
| 6,544,239 B2 * | 4/2003 | Kinsey et al. | 604/272 |
| 6,589,157 B2 * | 7/2003 | Fontayne et al. | 600/3 |
| 6,607,529 B1 * | 8/2003 | Jones et al. | 606/47 |
| 6,960,192 B1 * | 11/2005 | Flaherty et al. | 604/181 |
| 7,008,439 B1 * | 3/2006 | Janzen et al. | 606/213 |
| 7,214,206 B2 * | 5/2007 | Rue et al. | 604/19 |
| 7,604,647 B2 * | 10/2009 | Chen | 606/166 |
| 7,632,256 B2 * | 12/2009 | Mosler et al. | 604/349 |
| 7,766,924 B1 * | 8/2010 | Bombard et al. | 606/143 |
| 2002/0077599 A1 * | 6/2002 | Wojcik | 604/162 |
| 2003/0220617 A1 * | 11/2003 | Dickerson | 604/263 |

FOREIGN PATENT DOCUMENTS

| | | | | |
|---|---|---|---|---|
| WO | 9813091 | | 4/1998 | |
| WO | 9813092 | | 4/1998 | |
| WO | WO9813091 | * | 4/1998 | A61M 37/00 |
| WO | 0168168 | | 9/2001 | |
| WO | 2004/089458 | | 10/2004 | |

* cited by examiner

APPLICATOR FOR INSERTING AN IMPLANT

The invention relates to an applicator for inserting an implant, in particular a rod-like implant containing an active substance, under the skin of a human or animal, comprising a housing, a cannula extending from the housing, and a handle for grasping and maneuvering the applicator and the cannula during insertion of an implant.

Such an applicator is known in the art.

EP 0 304 107 discloses an injection device (denoted by numeral 1), in particular for once-only use, for injecting an implant (6) which can release a drug in a controlled manner, which device comprises a housing (2) which is provided at the injection end with an injection needle (3) in which the implant (6) can be disposed and in which a passage opening is disposed at the actuating end of the housing for a plunger (7,8), mounted in the housing and displaceable in the axial direction of the needle (3), which plunger, on the one hand, can interact with the implant (6) and, on the other hand, is provided with an actuating element, which element is constructed as an element (10) for pressing and supporting against or on the part of the body to be treated.

It is an object of the present invention to provide an improved applicator.

To this end, the applicator according to the present invention is characterised in that the handle extends above at least part of the length of the cannula, at least during insertion of the cannula. It is preferred that the handle extends above at least 30%, preferably at least 50% of the length of the cannula extending from the housing.

Such a handle appeared to facilitate insertion of the cannula and/or accurate positioning of the implant.

If the handle extends above at least 80% of the length of the cannula extending from the housing, insertion of the cannula at a proper angle is also facilitated.

To allow gentle lifting of the skin while (part of) the cannula is inserted, it is preferred that the width of the handle increases in a direction away from the cannula.

It is further preferred that the top surface of the handle is raised relative to the rest of the housing. As a result, a medical professional entrusted with inserting the implant will more or less intuitively grasp the applicator at the handle.

The applicator preferably comprises a cannula holder and a lever extending along at least part of the cannula, which lever is rotatable and/or slidable and/or flexible between a first position wherein the implant is secured inside the cannula and/or the cannula holder and a second position wherein the implant is disengaged. The advantages of such a lever will be discussed in more detail below.

In order to reduce the risk of causing distress to the patient, it is preferred that the lever, in its first position, at least partially covers the cannula.

For the sake of completeness, it is noted that WO 98/13092 discloses a tissue penetration guide (denoted by numeral 8), which limits the range of motion of a device (2) useful for making insertions under and substantially parallel to the surface of a particular tissue (10) or overlapping series of tissues such that the insertion is made to the desired depth. The tissue penetration guide according to WO 98/13092 comprises a substantially linear, preferably linear, extension of material maintained substantially parallel to, preferably parallel to, and separated from the extended portion of the device designed to make the insertion in question. The guide is designed to remain on or near the surface of tissue to be entered and guide the insertable portion of the device or instrument to its desired inserted position. WO 98/13091 discloses a similar penetration guide. The guides according to these publications are neither intended nor suitable for use as a handle.

U.S. Pat. No. 4,223,674 discloses an implant gun including a grip or handle (10), slidably connected to an intermediate member (12), and a hollow needle (16).

EP 596 161 discloses an apparatus for subcutaneous introduction of a needle (2) into a living being. Guiding means (4,5) are provided at both sides of the needle.

U.S. Pat. No. 1,655,158 discloses an instrument for implanting radon seeds which is composed of three elements, namely, an implanter (1), a trocar (2), and a plunger (3). The implanter comprises a tubular body portion (4) and a needle (5).

WO 2004/089458 discloses a device for inserting implantable objects beneath the skin of a patient which includes a handle for grasping the device and a base connected to the handle. The base comprises a post, a cannula, and a flexible actuator positioned in an angled track.

WO 01/68168 discloses a disposable device for inserting one or several implants, said device comprising a tubular cannula (10) provided with a tip (11), said cannula also serving as a container for the implants, a plunger (20), and a handle (30) having a first end (31) directed towards the cannula (10) and a second end (32) directed away from the cannula.

The invention will now be explained in more detail with reference to the drawings, which schematically show two preferred embodiments according to the present invention.

Figure 1:
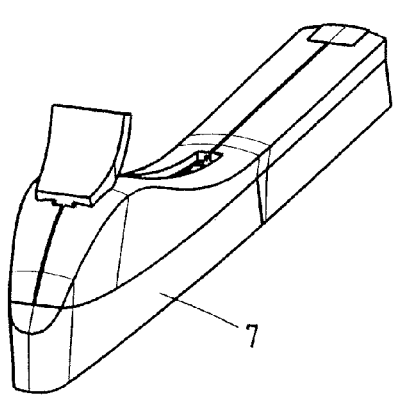
FIG. 1 is a perspective view of a first embodiment of an applicator in accordance with the present invention.
Figure 2:
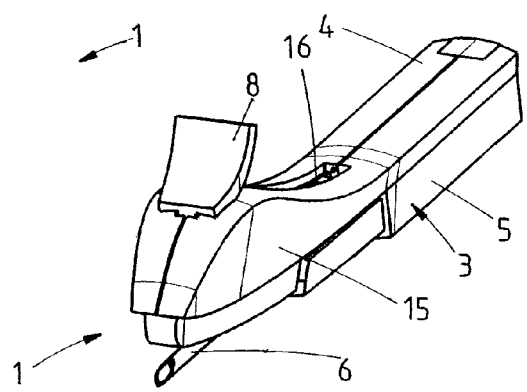
FIG. 2 is a perspective view of the same applicator as in FIG. 1, with its protective cover removed.
Figure 3:
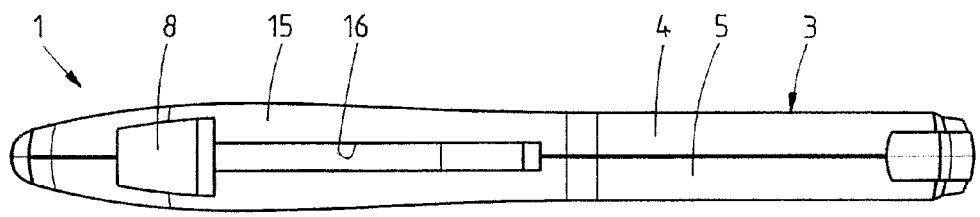
FIGS. 3 and 4 are, respectively, a top view and a cross-sectional side view of the preferred applicator of FIG. 1, with the cannula in an extended position.
Figure 4:
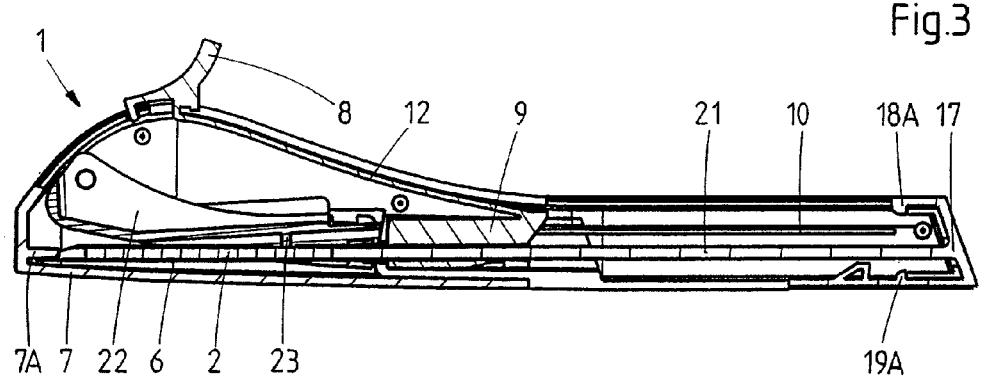
Figure 5:
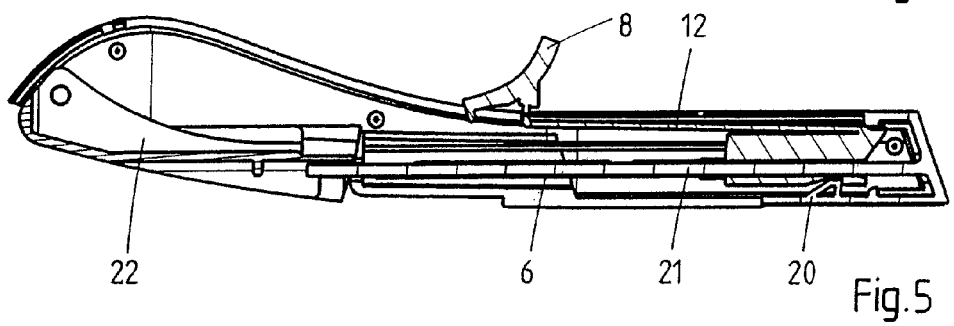
FIG. 5 is a cross-sectional side view of the preferred applicator of FIG. 1, with the cannula in a retracted position.
Figure 8:
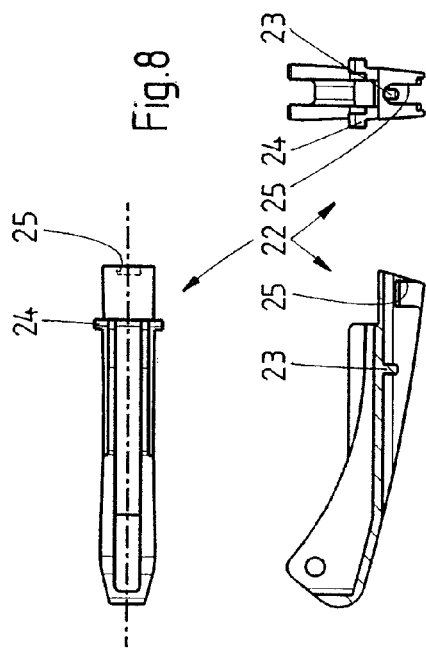
Figure 7:
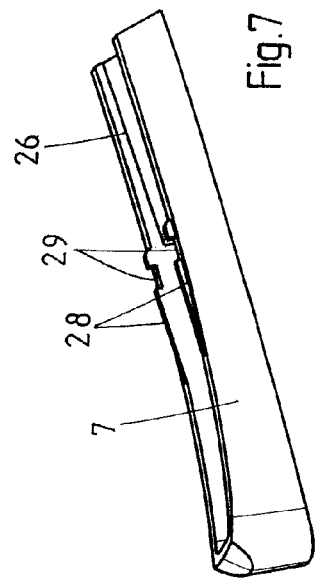
FIG. 7 is a perspective view of the protective cover.

FIG. 8 provides top, cross-sectional, and rear views of a lever used in the preferred applicator of FIG. 1.

Figure 9:
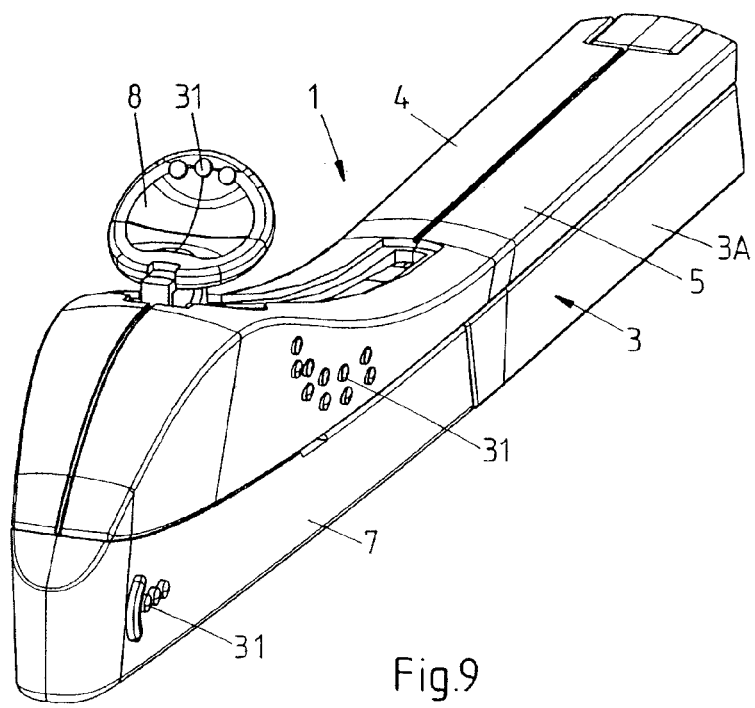

FIG. 9 is a perspective view of a second embodiment of an applicator in accordance with the present invention.

Figure 10:
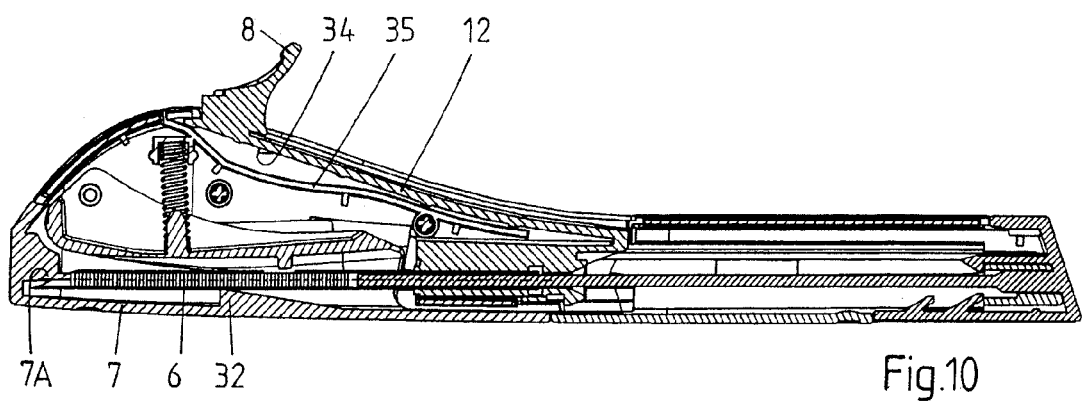

FIG. 10 is a cross-sectional side view of the preferred applicator of FIG. 9, with the cannula in an extended position.

Figure 11:
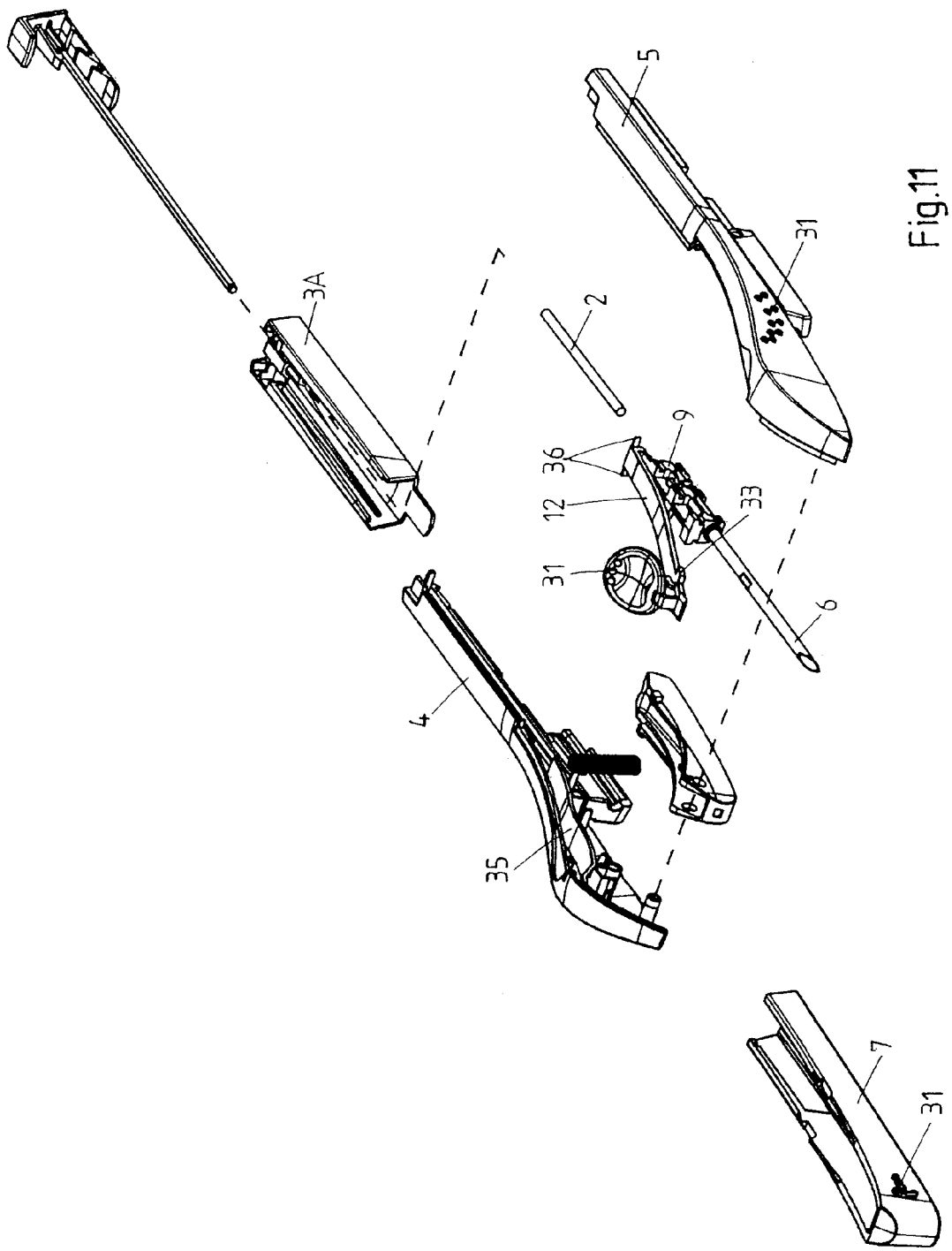

FIG. 11 is an exploded view of the preferred applicator of FIG. 9.

FIGS. 1 to 8 show a preferred disposable applicator 1 for inserting an implant 2, in particular a rod-like implant containing an active substance, such as a contraceptive, under the skin of a human. The applicator 1 comprises a housing 3 consisting of two half-shells 4, 5, a metal cannula 6 (FIG. 2) accommodating the implant 2, a protective cover 7 (FIGS. 1 and 4) comprising a pin 7A extending into the tip of the cannula 6 to restrict the freedom of movement of the implant 2, and an actuator 8 for retracting the cannula 6 into the housing 3. The cannula 6 is fixed to a cannula holder 9, which is slidably received inside the housing 3. To this end, the inner wall of each of the half-shells 4, 5 is provided with two parallel and longitudinal guides 10 (FIG. 6) and the cannula holder 9 is provided with corresponding longitudinal grooves 11. The cannula holder 9 is connected to the actuator 8 by means of a flexible element 12, which, in this example, forms an integral whole with the cannula holder 9 and the actuator 8. Using a flexible element to interconnect the actuator and the cannula holder provides improved freedom to the designer of the applicator in selecting the location of the actuator. I.e., the actuator can be located at a position that is convenient during insertion of an implant.

However, depending on the configuration of the applicator, it may be more advantageous to employ a rigid element and/or a separate actuator, flexible element, and needle holder which are connected upon assembly of the applicator.

Figure 6:
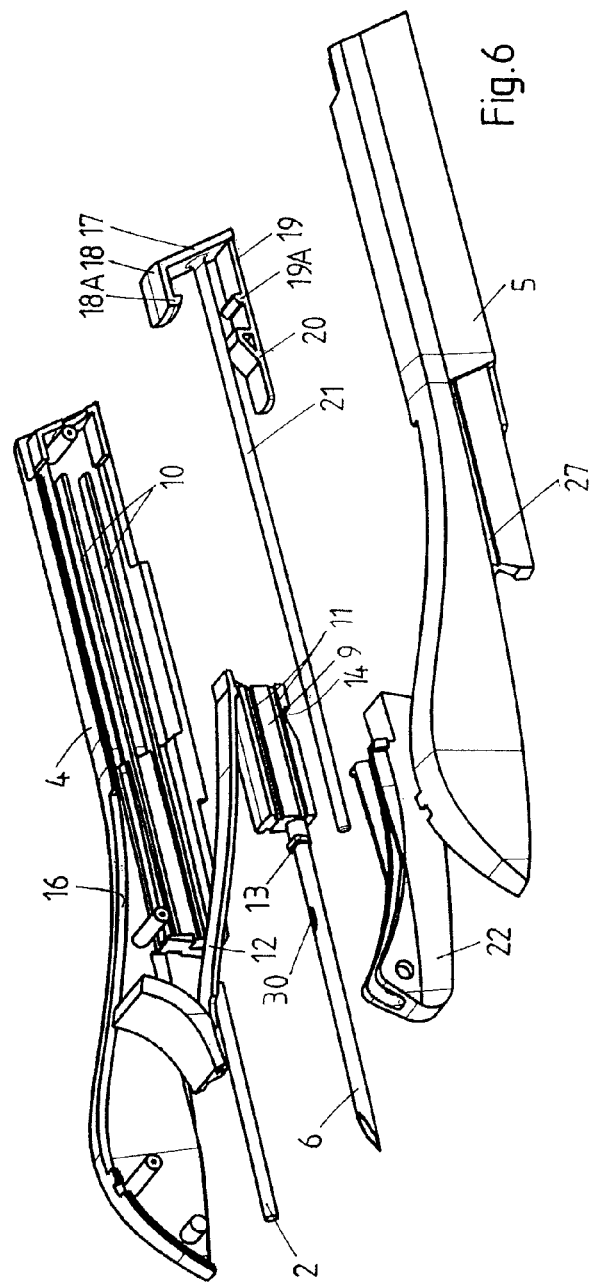
FIG. 6 is an exploded view of the preferred applicator of FIG. 1.

As can be seen in FIG. 6, the cannula holder 9 comprises a collar 13 on its front (distal) end, at the transition to the cannula 6, and a notch 14 on its bottom surface near its rear (proximal) end. As will be explained below, these features serve to lock the cannula holder, and hence the cannula, in an extended and a retracted position, respectively.

The housing 3 comprises a handle 15 for grasping and maneuvering the cannula 6 during insertion. The handle 15 extends above, i.e. along and spaced from the cannula 6, preferably to near the distal end of the cannula 6. To further enhance grasping the applicator and maneuvering the cannula, it is generally preferred that the thickness of the handle and/or the bending stiffness are greater than the thickness and the bending stiffness, respectively, of the cannula.

To allow gentle lifting of the skin while (part of) the cannula is inserted, the width of the handle 15 increases gradually in a direction away from the cannula 6. Maneuvering and lifting can be further improved by providing, on the handle 15, surface parts that have a relatively high coefficient of friction. Suitable materials for such surface parts include elastomers, which are preferably co-injection moulded along with the material of the housing itself. The top surface of the handle 15 is raised relative to the rest of the housing 3. As a result, a medical professional entrusted with inserting the implant will more or less intuitively grasp the applicator at the handle 15.

On top of the handle 15, a track 16 is provided for guiding the actuator 8. Guides (not present in this particular embodiment) may be included, preferably just below the track 16, to retain and guide the flexible element 12.

A bracket 17 has been inserted in and snap-fitted to the rear end of the housing 3, by means of two resilient fingers 18, 19, each provided with a protrusion 18A, 19A. The lower finger 19 further comprises, near its end, a wedge-shaped protrusion 20. The bracket 17 also comprises a rod 21, which extends through the greater part of the housing 3 and into the cannula holder 9 and the cannula 6. In this example, the length of the rod 21 is adjusted to the length of the lumen of the cannula holder 9 and the cannula 6 and the length of the implant 2, such that when the cannula 6 is in the extended position, the implant 2 is fully contained inside the cannula 6 and typically abuts the distal end of the rod 21. When the cannula 6 is in the retracted position, the implant 2 is completely expelled from the cannula 6 and the distal end of the rod 21 extends from the distal end of the (retracted) cannula 6.

A lever 22 has been pivotally connected to the front end of the handle 15. The lever 22 is gently biased towards the cannula 6 by means of a metal spring (not shown) extending between the lever 22 and an inner wall of the handle 15. In the present preferred example, the lever 22 interacts with the protective cover 7, the implant 2, and the cannula holder 9. To this end, the lever 22 comprises (from left to right in FIG. 8), a first protrusion 23 on its lower wall, a pair of lateral protrusions 24 on its upper rim, and a vertically extending slot 25 in its rear wall.

The protective cover 7 (FIG. 7) on its inner walls comprises a pair of ridges 26 which, in combination with corresponding slots 27 on the outside of the half-shells 4, 5, impose sliding engagement between the cover 7 and the housing 3. The cover 7 further comprises, on its upper rim, a pair of keys 28, each interrupted by a notch 29.

Finally, the cannula 6 comprises an opening 30 (FIG. 6) which allows the protrusion 23 to engage the implant 2 and thus to gently urge the implant 2 against the inner wall of the cannula 6.

With the protective cover 7 in place, the lateral protrusions 24 of the lever 22 are supported by the keys 28 and the first protrusion 23 is just clear of the implant 2.

If the protective cover 7 is removed, i.e. slid in longitudinal direction and away from the housing 3, the keys 28 will slide under the lateral protrusions 24. If no implant 2 is present inside the cannula 6, the protrusion 23 on the lever 22 is free to enter the cannula 6 through the opening 30. I.e., the lever 22 will drop when the lateral protrusions 24 reach the notches 29, thus blocking further movement of the cover 7, preventing the same from being removed and preventing the applicator from being used any further. If an implant 2 is present, the lever 22 will be lowered only very slightly, with the lateral protrusions 24 still clear of the notches 29, and yet causing the first protrusion 23 to rest, through the opening 30, on the implant 2, thus, on the one hand, allowing the cover 7 to be removed and, on the other, gently urging the implant 2 towards the inner wall of the cannula 6, i.e. securing the implant 2 inside the cannula 6.

A medical professional can now take the applicator 1 in one hand, e.g. with the thumb on one side of the handle 15 and the fingers on the other side, and insert the cannula 6 under the skin of a patient. During insertion, the handle 15 on the one hand prevents the cannula from being inserted at too large an angle and on the other enables coordinated maneuvering of the applicator 1 and the cannula 6 and careful lifting of the skin to facilitate insertion of the implant 2 at an appropriate depth. Skin on top of the cannula 6 will lift the lever 22 to such an extent that contact between the protrusion 23 and the implant 2 is removed, i.e. the implant 2 is disengaged without requiring a specific action by the medical professional, and the slot 25 in the rear wall of the lever 22 clears the collar 13 on the front portion of the cannula holder 9, thus unlocking the latter. Subsequently, the actuator 8 is unlocked and the cannula 6 is pulled rearwards, e.g. with the index finger of the hand that holds the applicator 1. During this rearward motion, the implant 2 abuts the distal end of the rod 21 and maintains its longitudinal position. Only limited friction occurs between the implant 2 and the inner wall of the cannula 6 and substantially no lateral forces are exerted on the implant 2. When the needle holder 9 arrives at the fully retracted position, the finger 19 (part of bracket 17) will flex downwards and the protrusion 20 on that finger 19 will snap into the notch 14 on the lower surface of the needle holder 9, preferably sounding an audible click and indicating to the medical professional that the implant 2 has been inserted and that the applicator 1 can be removed and discarded. The said protrusion 20 and notch 14 also form a lock that prevents the applicator 1 from being used again.

FIGS. 9 to 11 show a second embodiment of an applicator in accordance with the present invention. The main differences with the first embodiment will be discussed below. Elements that are at least substantially identical to those in the first embodiment are denoted by the same numeral.

In the second embodiment, the housing 3 consists of two side shells 4, 5 welded together (ultrasonically) and a separate rear section 3A, which has been snap fitted to the side shells 4, 5. The handle 15 and the protective cover 7 have been provided, on either side, with a relief, in this example a pattern of protrusions 31, to enhance grip and to provide (additional)

guidance as to where to grasp these respective parts 15, 7. Similar protrusions 31 have been provided on the (upper) rim of the actuator 8.

Further, the cover 7 comprises, on its inner bottom wall, a stay 32 preferably having, in its top surface, a V-shaped groove extending in the longitudinal direction of the applicator 1. Upon placing the protective cap 7 onto the housing 4, 5, the stay 32 slightly lifts the cannula 6 and reproducibly defines the lateral position and height of the tip of the cannula 6 with respect to the pin 7A, thus preventing contact between the tip of the needle and the inner walls of the cover 7.

The flexible element 12, interconnecting the actuator 8 and the cannula holder 9, comprises, preferably just below the actuator 8 and on either side of the flexible element 12, lateral protrusions 33. The inner wall of the housing 4, 5 in turn comprises two corresponding stops 34, which prevent the protrusions 33 from passing and hence the actuator 8 from being pulled rearwards unintentionally. The lateral protrusions 33 and stops 34 also prevent the cannula holder 9 and the cannula 6 from being pushed rearwards during insertion.

A guide 35 for retaining and guiding the flexible element 12 is provided just below the track 16. The guide 35 is shaped to provide sufficient room below the actuator 8 to enable it to flex sufficiently far downwards and allow the lateral protrusions 33 to pass the stops 34, upon pushing the actuator 8 down. Retracting the cannula 6 may thus be performed in one flowing movement, i.e. upon applying pressure to the actuator 8, typically with an index finger, the actuator 8 flexes downwards, clearing the stops 34, and subsequently moves rearwards to the retracted position.

In contrast to the first embodiment, no collar (13) is present on the front (distal) end of the cannula holder 9. Instead, two resilient lips 36 are provided on the rear (proximal) end of the cannula holder 9. The inner sidewalls of the housing 4, 5 in turn comprise two corresponding stops (not shown) that block rearward motion of the lips 33 and hence define the longitudinal position of the cannula holder 9 in rearward direction. It is preferred that this mechanism urges the cannula holder 9 into its most forward position, so as to prevent the implant 2 from extending from the cannula 6. Upon actuation, the lips 33 will flex inwards and past the stops.

As will be clear from the explanations above, the applicator according to the present invention facilitates insertion of the cannula and/or accurate positioning of the implant. Hence, the applicator according to the present invention is especially suitable for use with implants that slowly release an active substance over an extended period of time. A preferred example of such an implant is a single-rod contraceptive implant that provides protection against pregnancy for an extended period of time, e.g. 3 years. It consists of a non-biodegradable rod measuring 40 mm in length and 2 mm in diameter. After insertion, the rod slowly releases a progestogenic hormone, viz. etonogestrel.

The invention is not restricted to the above-described embodiments, which can be varied in a number of ways within the scope of the claims. For instance, the actuator can be located on or in a sidewall of the handle instead of on top of the handle.

The invention claimed is:

1. Applicator for inserting an implant under the skin of a human or animal, comprising a housing, a cannula having an insertion length extending outside the housing, a rod extendable at least partially inside the cannula, and a handle for grasping and maneuvering the applicator and the cannula during insertion of an implant, wherein at least a portion of the housing is cantilevered over the cannula to form the handle, which cantilevered portion of the housing extends along in spaced, substantially parallel relation to at least part of said insertion length that extends outside the housing and said cantilevered portion of the housing has a width in a direction perpendicular to the insertion length of the cannula, said width of said cantilevered portion increasing over at least part of the cantilevered portion in a direction along the insertion length of the cannula to form respective side surfaces, said width being substantially larger than a diameter of the cannula to enable the handle to be gripped by a user, and wherein the cannula is retractable into the housing by sliding the cannula relative to the rod for expelling the implant.

2. Applicator according to claim 1, wherein the handle extends along at least 30% of said length.

3. Applicator according to claim 1, wherein a top surface of the handle is raised relative to the rest of the housing.

4. Applicator for inserting an implant under the skin of a human or animal, comprising a housing, a cannula having an insertion length extending outside the housing, a handle for grasping and maneuvering the applicator and the cannula during insertion of an implant, a cannula holder, a rod mounted on or in the housing and at least partially inside the cannula or the cannula holder, and an actuator for sliding the cannula and the rod relative to each other, wherein at least a portion of the handle is cantilevered above the cannula and located to extend along in spaced, substantially parallel relation to at least part of said insertion length that extends outside the housing and wherein the actuator is located on said cantilevered handle portion and moveable with respect to the cantilevered handle portion for sliding the cannula.

5. Applicator according to claim 4, wherein, when an implant is present in the cannula, the actuator is located over the cannula.

6. Applicator according to claim 4, wherein the cannula holder is provided at a proximal end of the cannula and is slidable over the rod, and wherein the actuator and the holder are interconnected by a flexible element.

7. Applicator according to claim 6, wherein the flexible element is at least partially retained by guides.

8. Applicator according to claim 1, comprising a lever extending along at least part of the cannula, which lever is rotatable or slidable or flexible between a first position wherein the implant is secured inside the cannula or the cannula holder and a second position wherein the implant is no longer secured inside the cannula.

9. Applicator according to claim 8, wherein, in its first position, the lever at least partially covers the cannula.

10. In combination, an implant for insertion under the skin of a human or animal, and an applicator, the applicator comprising a housing, a cannula having an insertion length extending outside the housing, and a handle for grasping and maneuvering the applicator and the cannula during insertion of the implant, wherein the handle has a portion that extends along in spaced, substantially parallel relation to at least 80% of said entire cannula length that extends outside the housing and said handle portion has a width in a direction away from the cannula that is substantially greater than a thickness of the cannula enabling the handle portion to be gripped by a user, wherein the implant is an elongate rod-like element containing an active substance.

11. The combination according to claim 10, wherein the handle has side surfaces enabling the handle to be gripped by a user.

12. The combination according to claim 10, wherein a bending stiffness of said portion of the handle is greater than that of the cannula.

13. The combination according to claim 10, wherein prior to use, the implant is located within the cannula and secured against accidental removal therefrom.

14. The combination according to claim 13, wherein the implant is secured against accidental removal by a protrusion extending into the cannula, insertion of the cannula under the skin causing release of the implant by the protrusion.

15. The combination according to claim 10, further comprising a cannula holder, a rod mounted to the housing and extending at least partially inside the cannula or the cannula holder, and an actuator for sliding the cannula and the rod relative to each other.

16. The combination according to claim 15, wherein the cannula holder is provided at a proximal end of the cannula and is slidable over the rod, and wherein the actuator and the holder are interconnected by a flexible element.

17. The combination according to claim 10, wherein the active substance is a progestogenic hormone.

18. Applicator for inserting a rod-like contraceptive implant containing a progestogenic hormone, under the skin of a human or animal, comprising:
   a housing;
   a cannula having an insertion length extending outside the housing prior to use and during insertion of the implant under the skin, said cannula being movable with respect to the housing to enable retraction of the cannula by the user into the housing during use;
   an implant retained within the cannula prior to use;
   a rod for expelling the implant from the cannula when the cannula is retracted; and
   a handle for grasping and maneuvering the applicator and the cannula during insertion of the implant, wherein the handle extends along and is spaced from at least part of said cannula insertion length outside the housing in said prior to use position and during insertion of the implant.

19. The applicator according to claim 18 wherein the implant contains etonogestrel and measures 40 mm in length and 2 mm in diameter and wherein the handle extends along and spaced from substantially all of said length.

20. Applicator for inserting an implant under the skin of a human or animal, comprising a housing having a distal end, a proximal end and a hollow interior, a cannula extending from the interior of the housing at an intermediate position between the distal end and the proximal end and extending towards the distal end of the housing, a rod extendable into the cannula, the cannula being slidable relative to a rod for expelling the implant, wherein the housing comprises a handle portion for grasping and maneuvering the applicator and the cannula during insertion of an implant, the handle portion being provided on the housing between the intermediate position and the distal end and having respective side surfaces enabling the handle portion to be gripped by a user, the handle portion extending in spaced relation to the cannula along an insertion length of the cannula outside the housing, the side surfaces of the handle portion between the intermediate position and the distal end having a width in a direction perpendicular to said insertion length of the cannula, said width being substantially larger than a diameter of the cannula.

* * * * *